(12) United States Patent
Bhatia et al.

(10) Patent No.: US 8,253,573 B2
(45) Date of Patent: Aug. 28, 2012

(54) ALARM UNIT FOR MONITORING OR DETECTION OF AN ANALYTE

(76) Inventors: Saket Subash Bhatia, Santa Clara, CA (US); Darrell Eugene Davis, Sunrise, FL (US)

( * ) Notice: Subject to any disclaimer, the term of this patent is extended or adjusted under 35 U.S.C. 154(b) by 338 days.

(21) Appl. No.: 12/661,823

(22) Filed: Mar. 25, 2010

(65) Prior Publication Data

US 2011/0234400 A1 Sep. 29, 2011

(51) Int. Cl.
*G08B 23/00* (2006.01)
(52) U.S. Cl. .................... 340/573.5; 340/540; 340/573.1
(58) Field of Classification Search .................. 340/540
See application file for complete search history.

(56) References Cited

U.S. PATENT DOCUMENTS

| | | | | |
|---|---|---|---|---|
| 5,036,859 A | * | 8/1991 | Brown | 600/547 |
| 2004/0207530 A1 | * | 10/2004 | Nielsen | 340/604 |
| 2005/0001728 A1 | * | 1/2005 | Appelt et al. | 340/573.1 |

* cited by examiner

*Primary Examiner* — George Bugg
*Assistant Examiner* — Kerri McNally
(74) *Attorney, Agent, or Firm* — Patent Jurist; Georgiy L. Khayet

(57) ABSTRACT

An alarm unit for monitoring or detecting presence of an analyte on a separate sensor portion. The present invention comprises only the alarm unit and its means for attachment to a user's clothing. A square plastic casing protects the alarm electronics portion including a signal processing means. A large clip attachment means is included that is easily separated and attached from the casing and is used to attach the unit to clothing and which has enough clearance to be used with thick articles of clothing including diapers and which has a set of teeth frictionally held against a rubber strip portion located on the casing back so as to also enable secure attachment to very thin articles of clothing. A three-way switch is located externally for easy alarm chime and alarm volume selection. Interdependent modes of operation enable the signal processing means to control the alarm unit operation and features including low power indication, improper cable plug installment, three-way switch deactivation during Monitor mode, and a snooze/reset feature by which the alarm is easily disabled temporarily so that, as an example, a user can focus on running to the bathroom where the device is used to treat enuresis.

8 Claims, 14 Drawing Sheets

ALARM UNIT FOR MONITORING OR DETECTION OF AN ANALYTE

CROSS REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates to devices that alarm and/or monitor the presence of analytes including but not limited to urine. More specifically, but not exclusively, the present invention relates to devices for treating enuresis. More specifically, the present invention relates to the electronics portion of enuresis alarms including the signal processing portion, the casing surrounding said electronics portion and the means for attaching said casing to articles of clothing in use.

2. Description of Related Art

The use of a urine sensor connected by an electrical cable to an electronics portion, that may utilize a signal processing unit, for the purpose of treating enuresis is well known in the prior art. Electrolytes present in urine close an alarm circuit thereby indicating micturition. Commonly, the electronics portion comprises an alarm unit that sounds an alarm and/or vibrates which wakes nocturnal enuresis sufferers. With time, constant waking at the point of micturition enables training the nervous system of the user so as to learn the sensation of needing to urinate. The electronics portion is contained within a casing that is attached to an item of clothing near the user's collarbone.

The prior art is filled with various solutions for attaching the alarm casing to the user's clothing. Malem Medical of Nottingham, England offers a safety pin permanently attached to the casing. The Dri-Sleeper Excel of New Zealand (described in US 2008/0246620 to Page) offers a hook and tab arrangement which requires each user to sew corresponding hook or tab strips to articles of clothing. US 2005/0110644 to Abramson et al. offers a magnet attached to a flexible arm that extends around a portion of clothing and attaches to a corresponding magnet on the back of the casing.

The above solutions offer functional solutions, however, each suffer from considerable disadvantages. A safety pin can become dangerously dislodged and must be cautiously attached every time. Sewing hook or tab strips to clothing presents a robust but laborious solution; adhesively attaching the corresponding hook or tab to the alarm is not a robust solution. The safety pin and hook and tab solutions also cause the mass of the alarm casing to pull down on the clothing article causing discomfort. The magnet and arm solution is able to utilize the neck opening of a pajama top for example and does not cause uncomfortable pulling on the clothing by virtue of being supported by the neck opening which is supported by the neck of the wearer. Having a strong magnet located in the alarm casing poses special problems however. The above magnetic arm solution to Abramson et al places the controls to the unit inside the alarm casing behind the batteries. Removing the battery door can cause batteries to dislodge and adhere tenaciously to the magnet in the housing making access to the controls difficult. The hook and tab and magnetic arm solution also do not allow for use with a disposable diaper.

The Malem Alarm and Dri-Sleeper Excel (US 2008/0246620 to Page) also place alarm controls inside the alarm casing, presumably exchanging ease of use for the prevention of intentional or unintentional changes to control settings by the user during sleep or alarm event. Indeed, the above US 2008/0246620 to Page requires the user to bridge pins in the circuit board to short out a capacitor in order to cause a change to the frequency of sound.

In use, many prior art sensor and alarm unit enuresis devices permit disabling of the alarm by simply pulling out the cable attaching the sensor to the alarm unit. This has the serious disadvantage of a sleepy child easily disabling the alarm instead of waking up to clean the sensor and change their underwear and curtails the benefit of alarm therapy. The Malem device above and the Wet-Stop3 offer a two step shut off feature requiring a sleeping child or other user wake up and remember how to disconnect the sensor plug and then to hold down a reset button for several seconds while the alarm sounds near the ear. This somewhat traumatic wakening distracts the user from focusing on sensations associated with the need to urinate and running to the bathroom to help form the association.

Use of passive electronics at night, whereby the closing of a circuit that activates an electronics unit is done passively as a result of involuntary nocturnal urination, poses special problems. One such problem is knowing if the electronics are operating properly, especially an issue for the child user. The prior art in enuresis alarms is void of features that actively confirm whether the sensor is inserted properly or whether the batteries are of insufficient power to operate the alarm. The above disadvantages may result in continual use of a non-functioning enuresis alarm and dissatisfaction and eventual rejection of alarm therapy and lead to potential misdiagnosis for the cause of enuresis.

SUMMARY OF THE INVENTION

The present invention overcomes the above disadvantages presented by the prior art. A large detachable plastic clip allows for easy frictional attachment and removal to the shirt collar. Said clip offers enough clearance to be attachable to a thick diaper as needed and is easily replaced if broken. Detaching the clip also enables use of alternative attachment means by exposing the casing back. A large external three-way switch extends outside the housing, is easy to use and is protected by a plastic guard portion. Four interdependent power state modes are employed by a signal processing means to control unit operation.

A Power Up mode is employed whereby a low power indicator means confirms remaining battery power is sufficient to power the alarm. The signal processing means then enters the Alarm Setup mode where the three-way switch is employed to set alarm chime type and alarm volume whereby a zero volume setting results in vibrate and flashing light only alarm setting. A switch means located in the electrical jack indicates via an alarm means that the cable plug leading to the analyte sensor portion has been properly inserted. The three-way switch is deactivated by the signal processing means after all alarm settings are set in Alarm Setup mode and upon entering Monitor mode. Upon detection of an analyte, the signal processing means enters Alarm mode whereby a pair of LED lights flash in synchronization with the alarm vibrate and audible alarm per the chime type and volume settings made in Alarm Setup mode. During Alarm mode a snooze reset button may be employed allowing the suddenly awakened user to perform one quick simple step to temporarily disable the alarm. The alarm is disabled for a short period of time making the alarm experience less traumatic and giving the user enough time to go to the bathroom to urinate, clean the sensor and reset the alarm. The present invention also offers publicly available prior art features such as electrode isolation whereby power is cut off to a sensor unit after detecting urine to prevent dangerous urine electrolysis (see U.S. Pat. No. 4,356,479 to Wilson) and alarm lighting, vibration and alarm chime type select and amplification, all of which are well known in the art.

The characteristics and utilities of the present invention described in this summary and the detailed description below are not all inclusive. Many additional features and advantages will be apparent to one of ordinary skill in the art given the following drawings, specifications and claims.

(BRIEF) DESCRIPTION OF THE DRAWINGS

The present invention may be better understood, and its numerous features and advantages made apparent to those skilled in the art by referencing the accompanying drawings. For ease of understanding and simplicity, common numbering of elements within the illustrations is employed to identify an element in the different drawings.

Figure 1A:
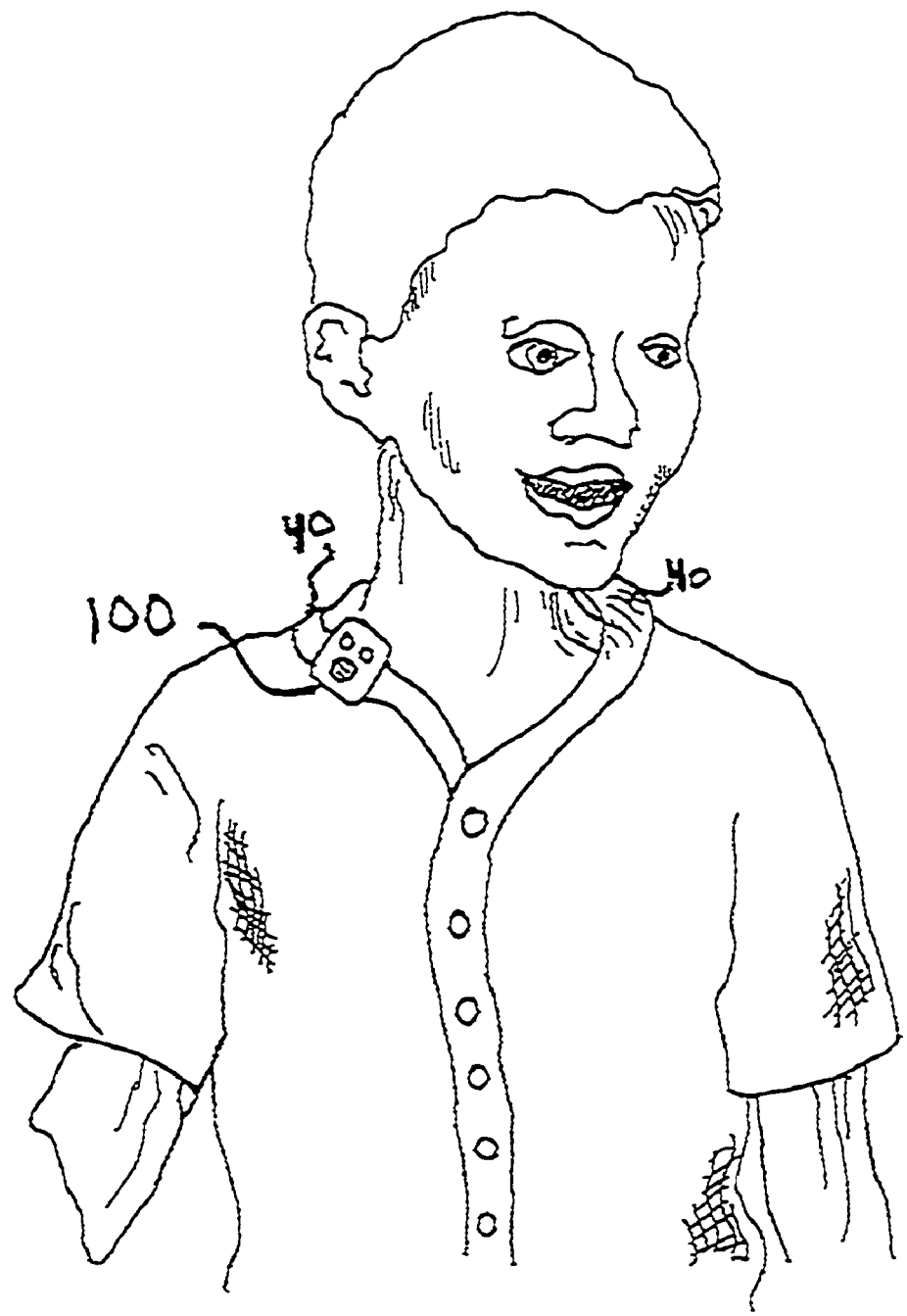
FIG. 1A shows a plain view of the front of the present invention as it appears attached to a user's pajama collar.
Figure 1B:
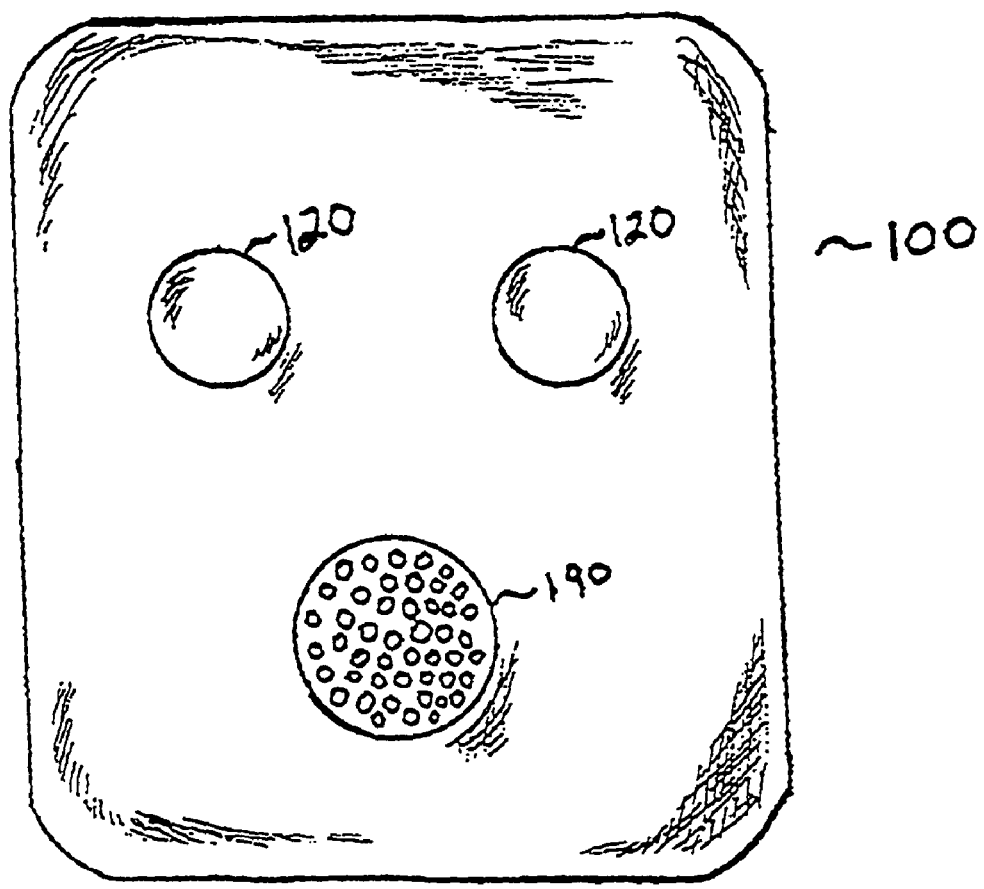
FIG. 1B shows a plain view of the front face of the present invention.
Figure 2:
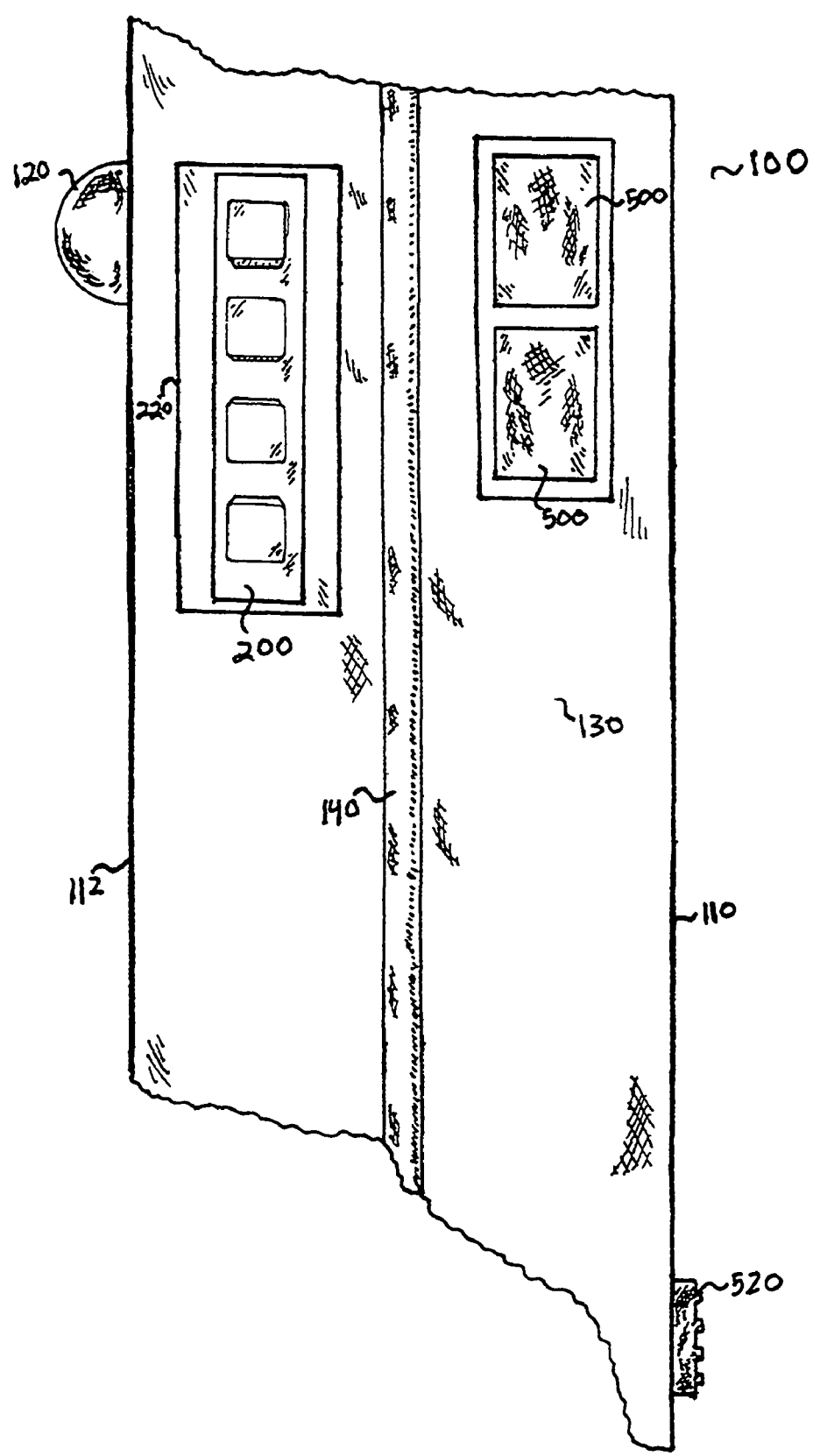
FIG. 2 is a partial side view of the casing displaying the mostly recessed three-way switch handle, an LED light housing, a clip means attachment point and a silicone or rubber strip portion.
Figure 3:
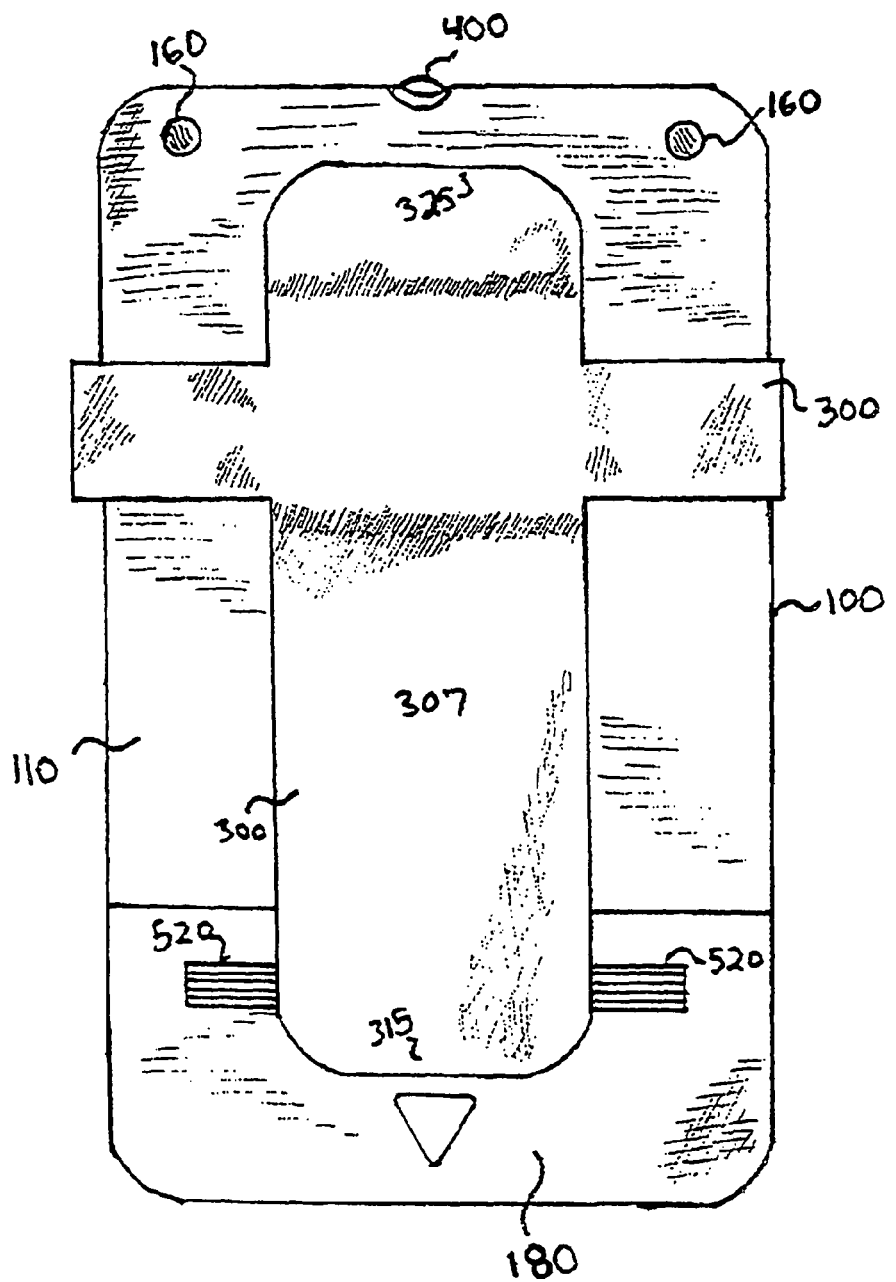
FIG. 3 is a plain view of the back of the present invention with the clip means affixed.
Figure 4A:
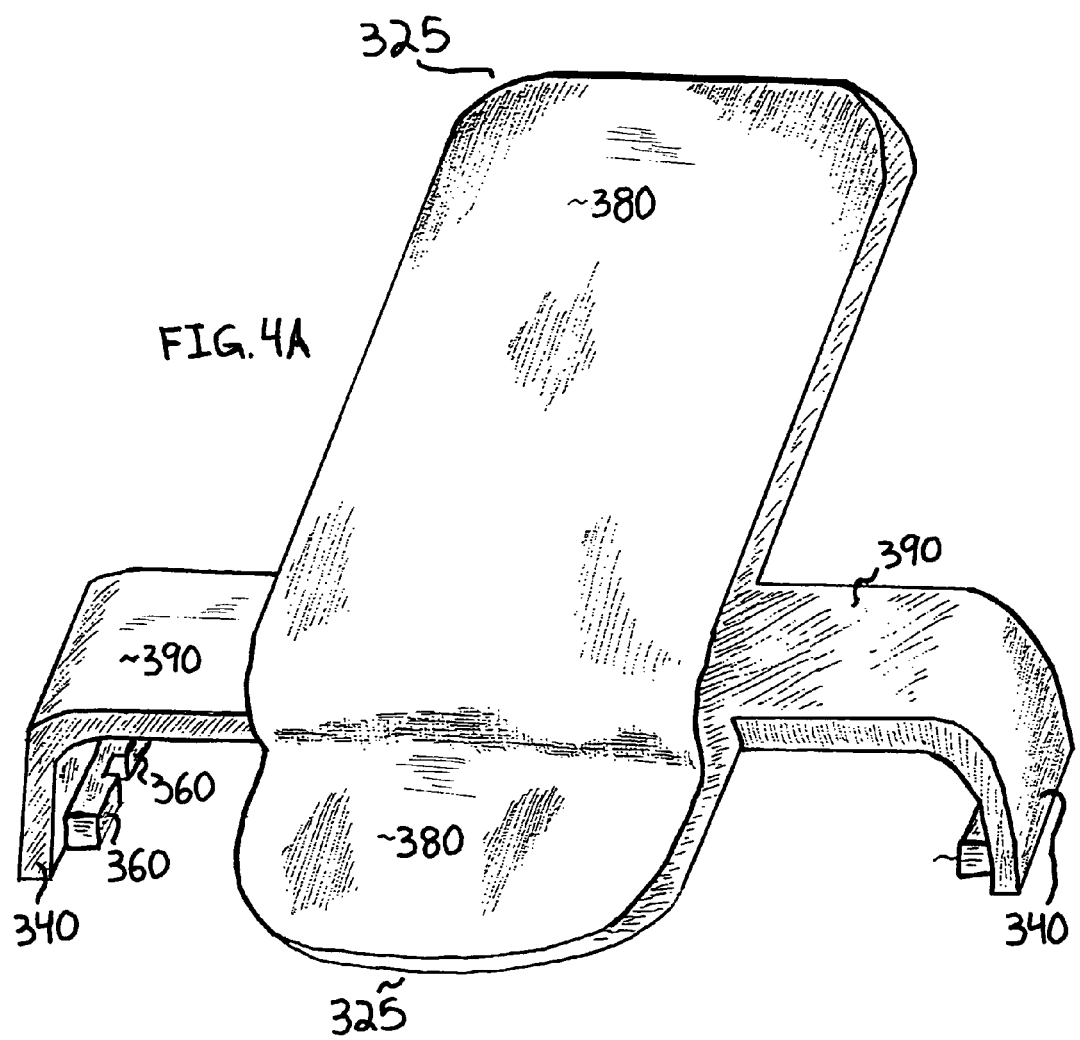
FIG. 4A is a perspective view of the outer side of the clip means.
Figure 4B:
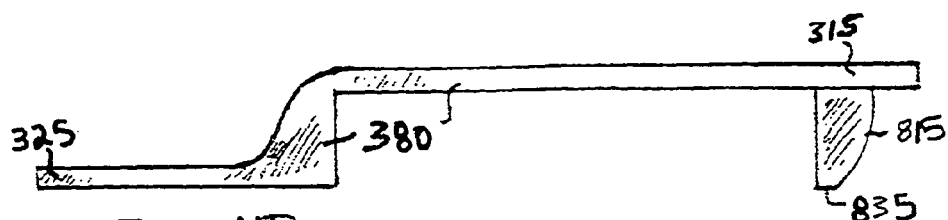
FIG. 4B is a side view of the clip main body portion.
Figure 4C:
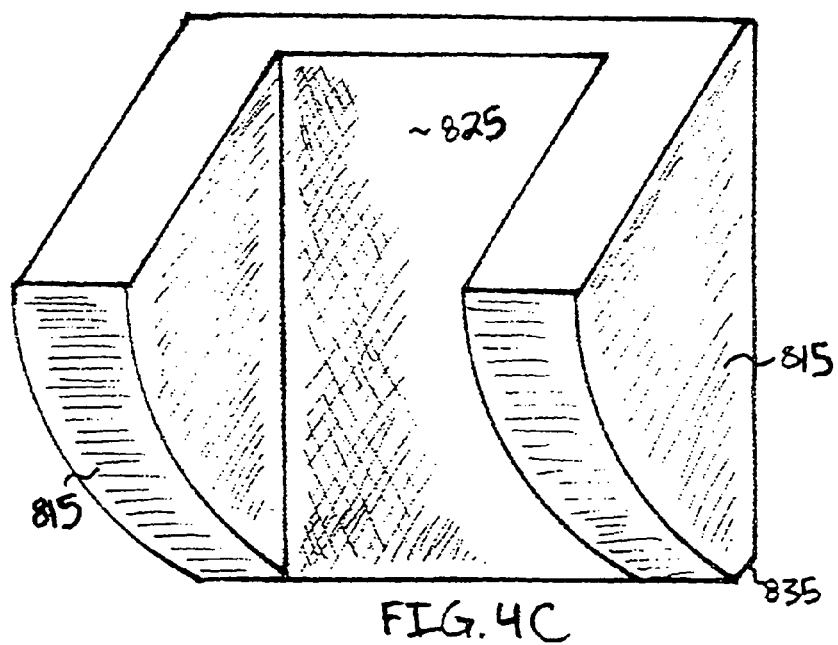
FIG. 4C is an isolated perspective view of the tooth and bridge portion unattached to the clip main body lower end.
Figure 4D:
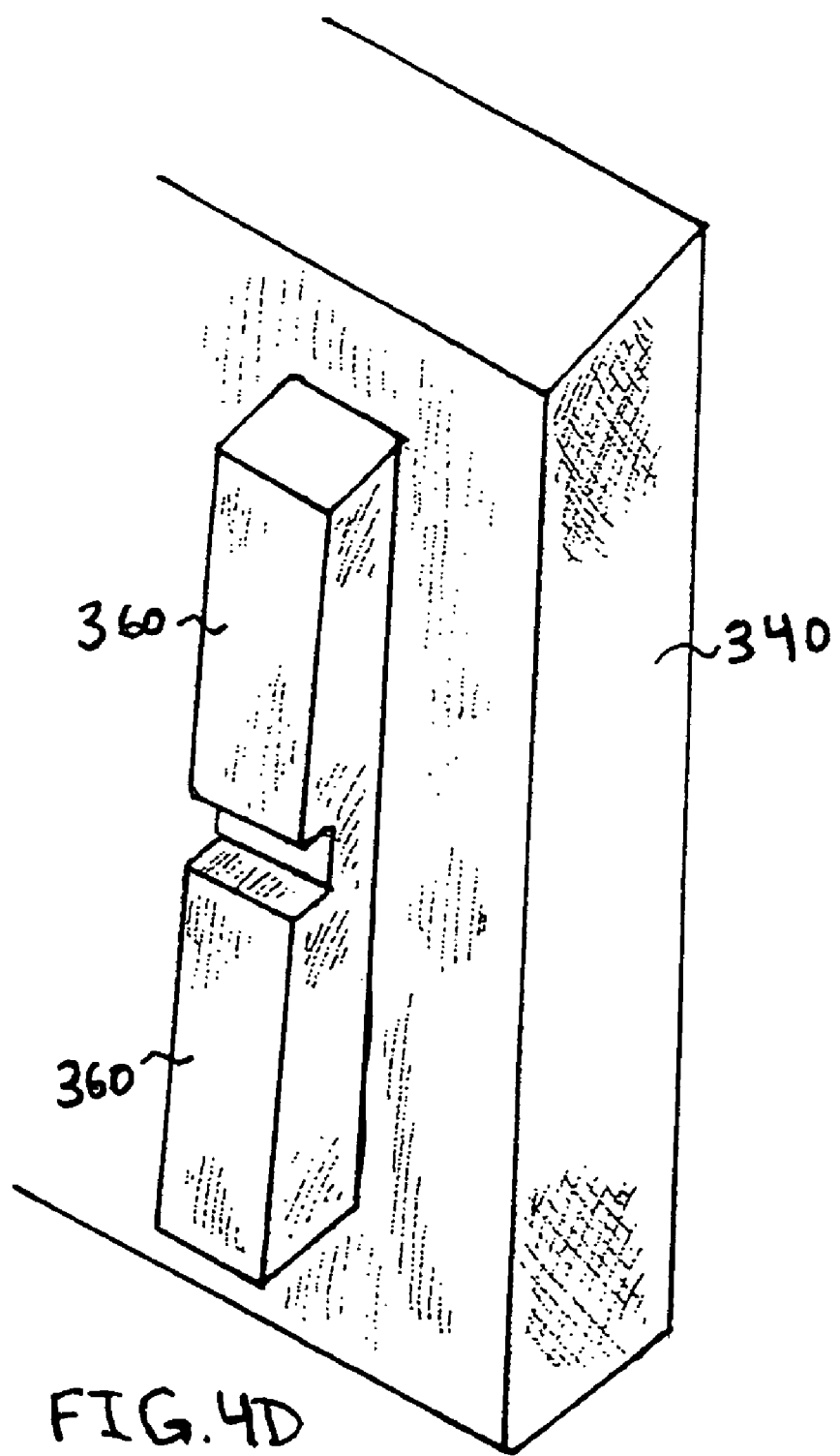
FIG. 4D is a perspective view of an attachment arm with tab portions.
Figure 5A:
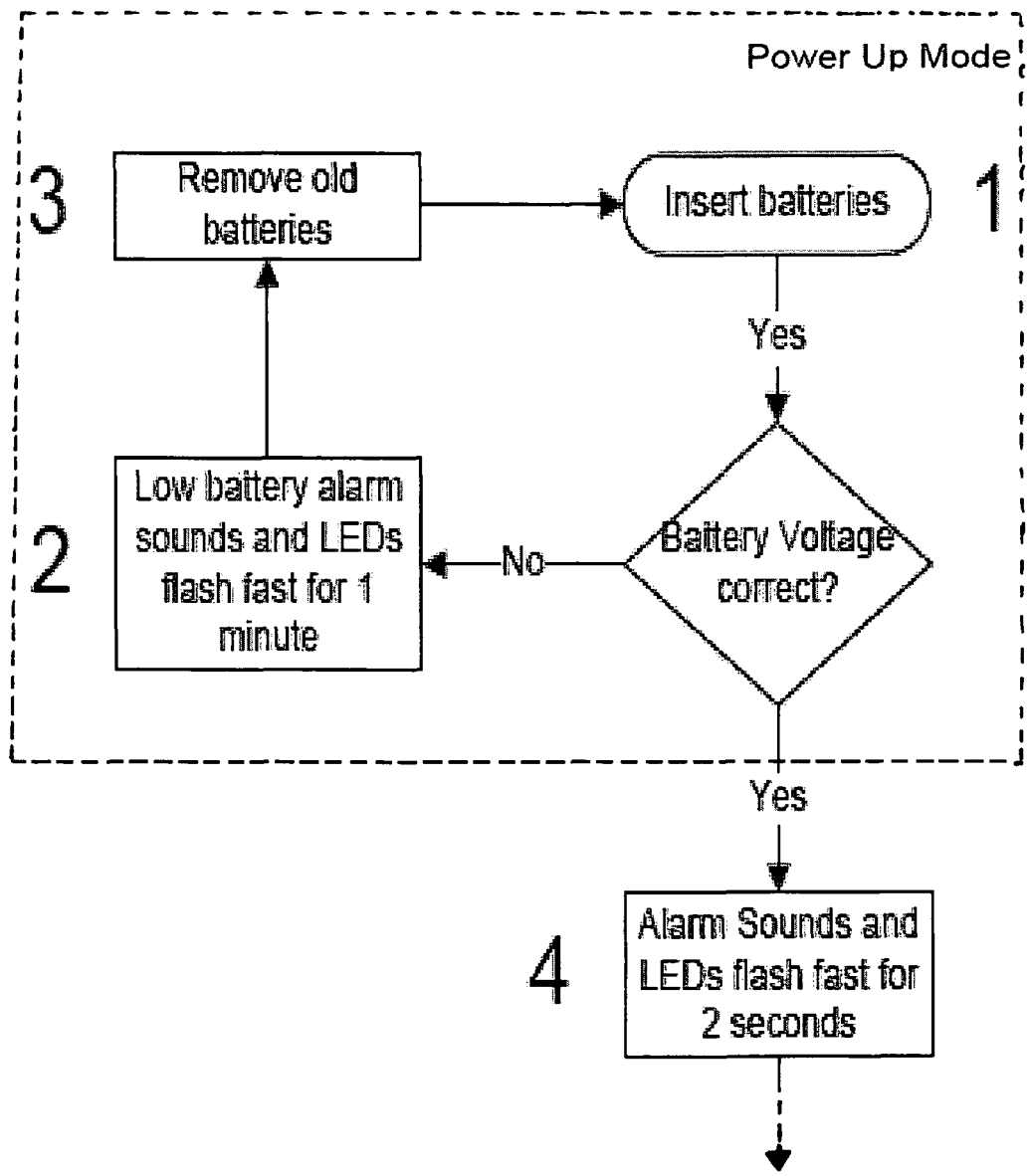
Figure 5B:
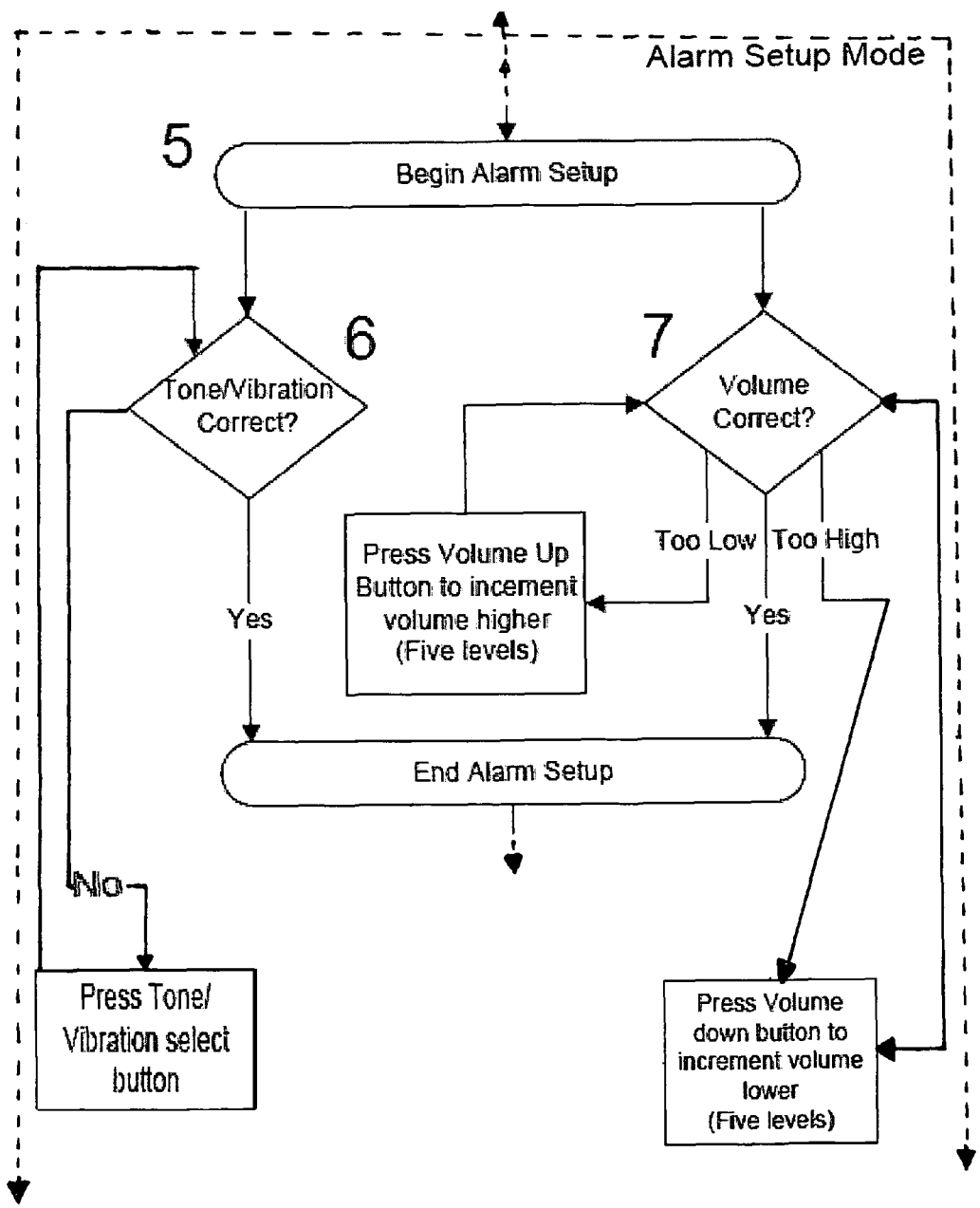
Figure 5C:
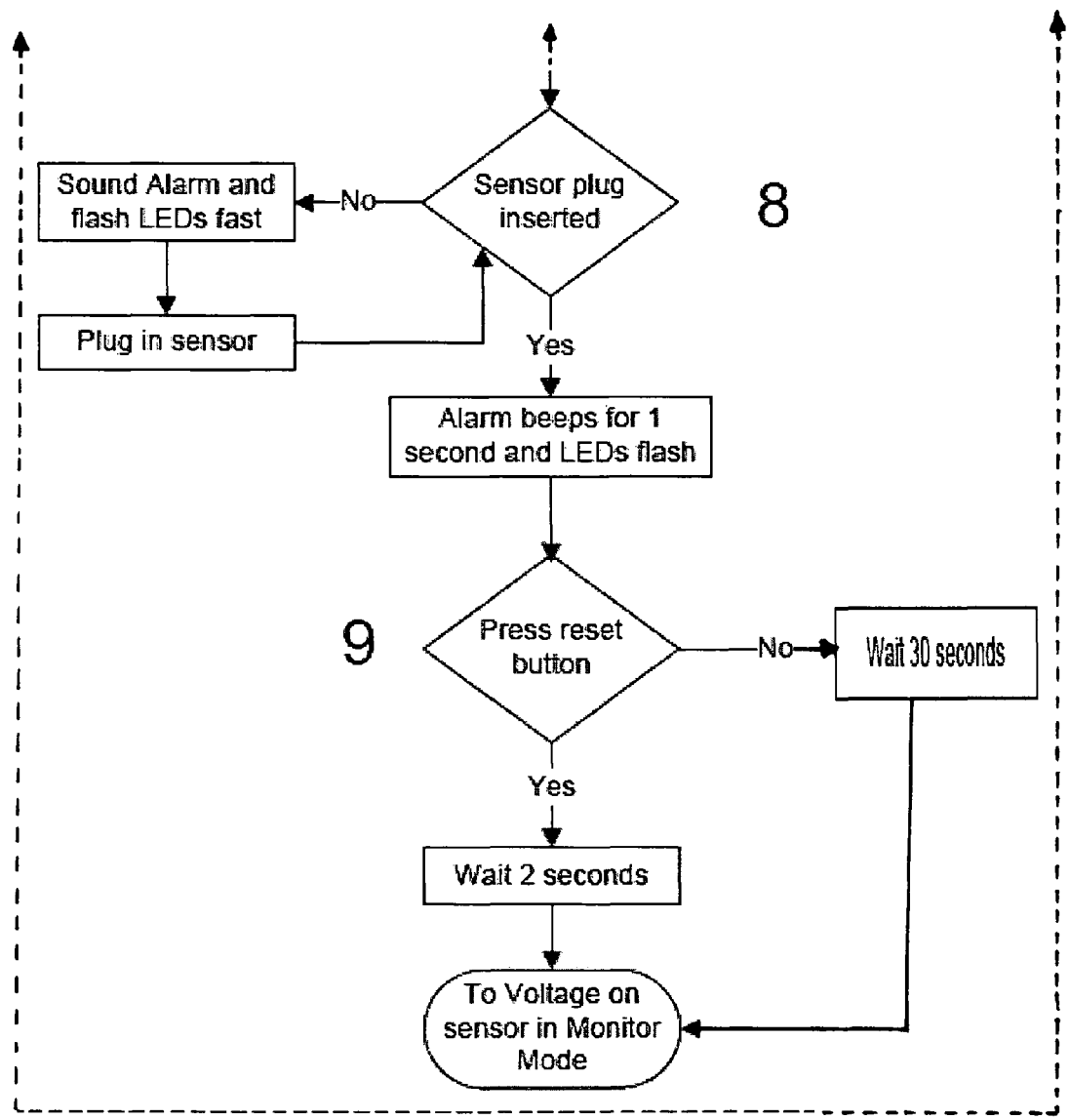
Figure 5D:
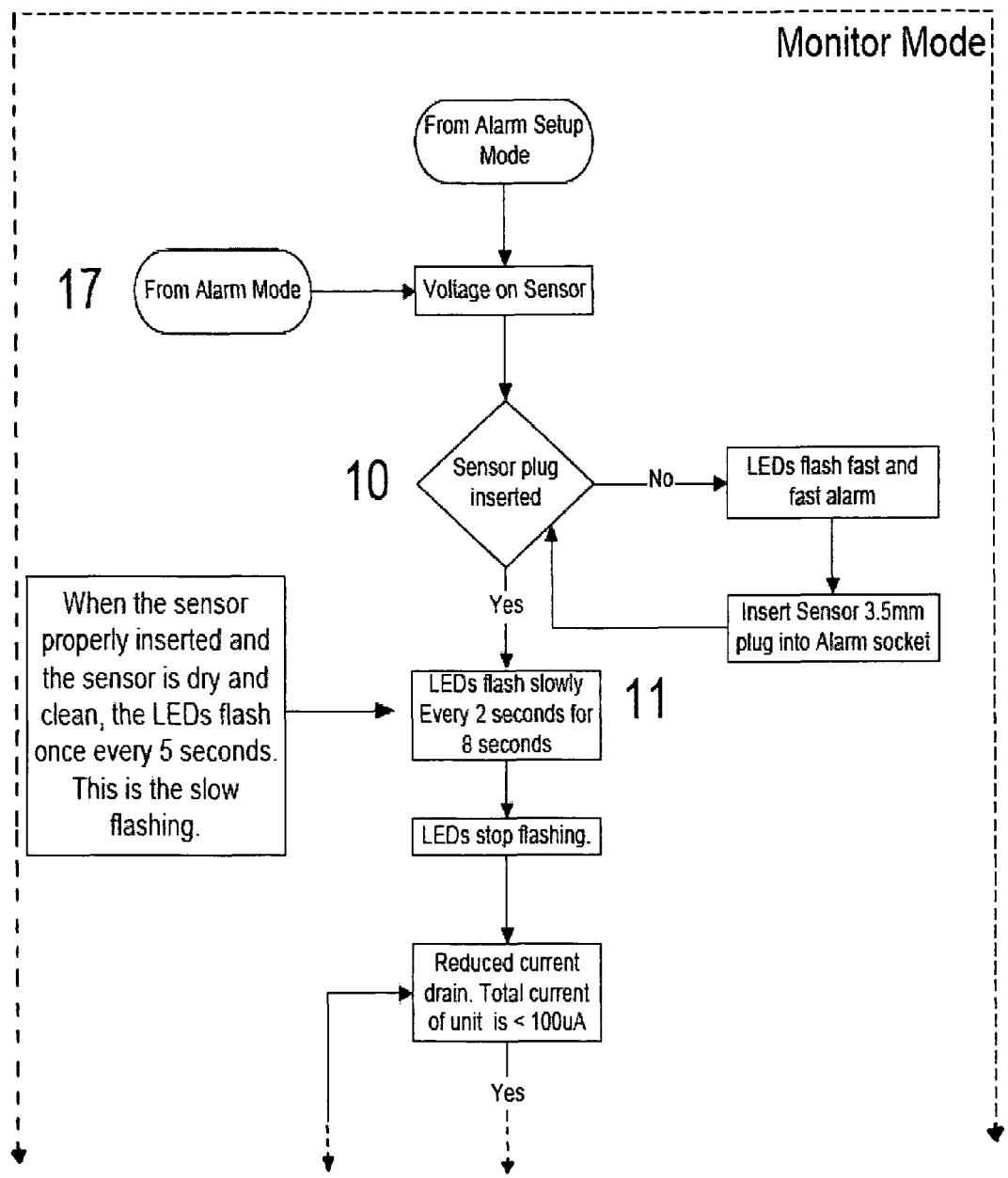
Figure 5E:
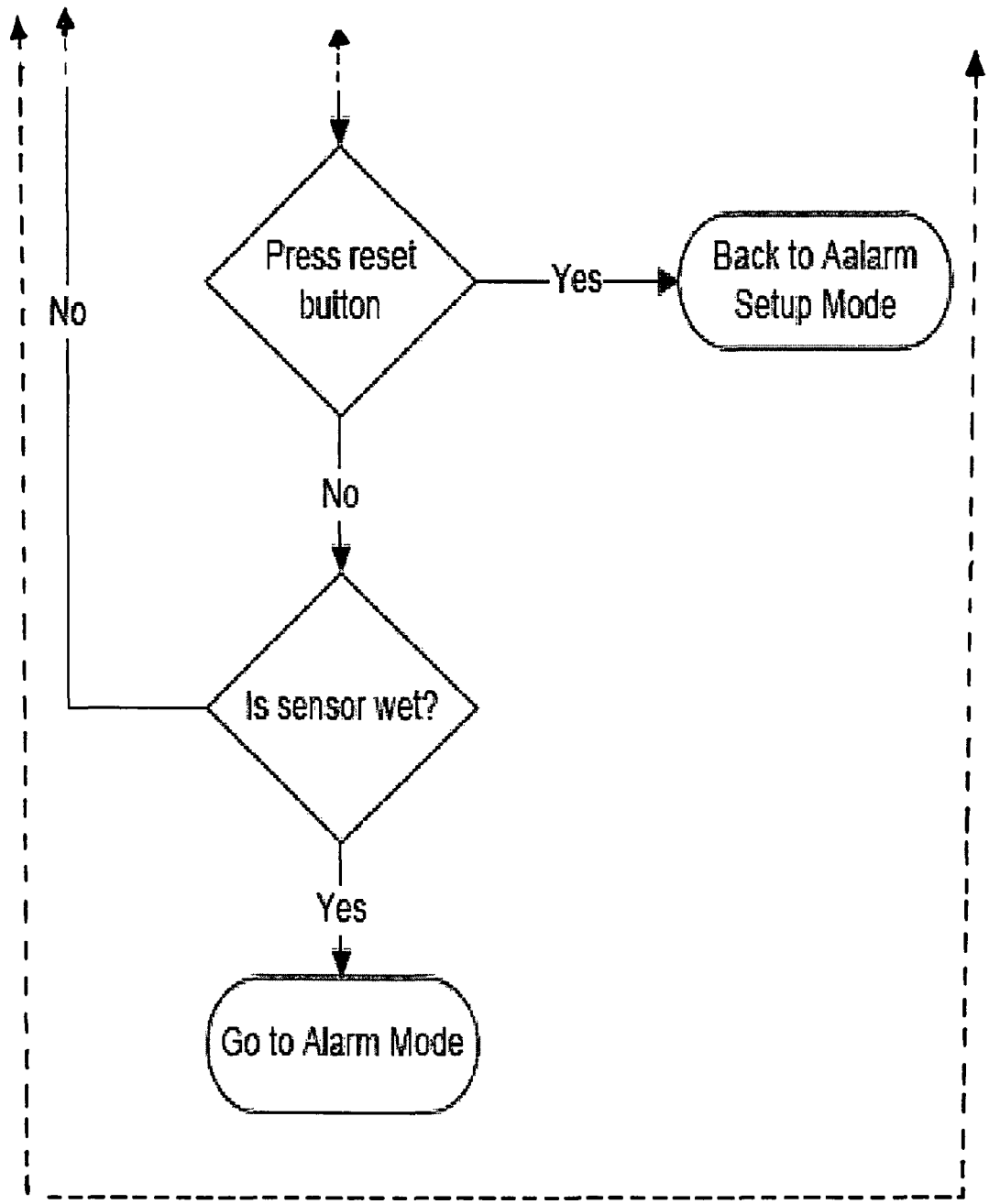
Figure 5F:
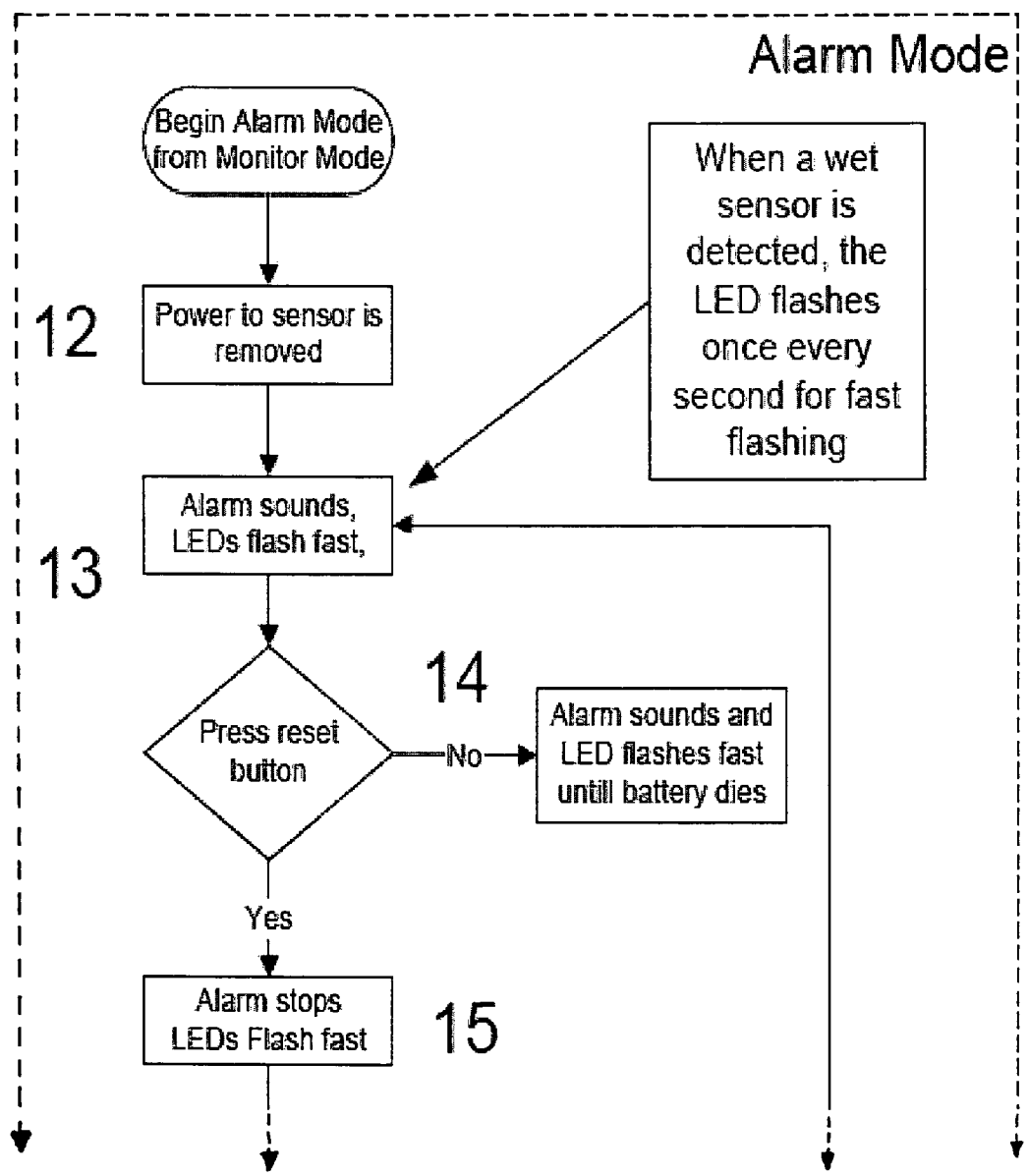
Figure 5G:
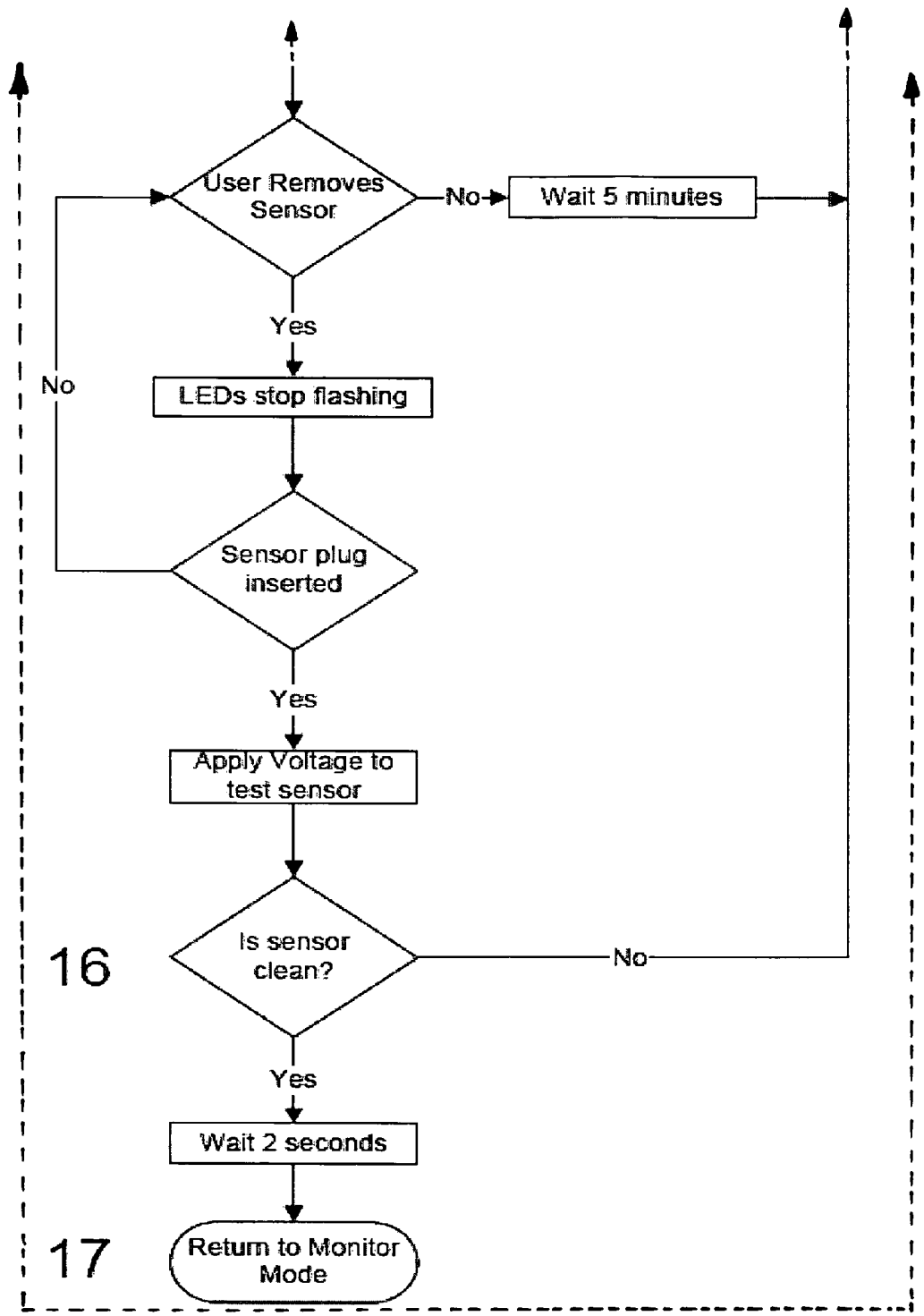

FIGS. 5A-G is shown on sheets 8-14 and is a flowchart diagram depicting the modes of operation and the power state modes. The power state numbering, indicated in FIGS. 5A-G by numerals 1-17, is defined below:

FLOWCHART POWER STATE NUMBERING DEFINITIONS

Power Up Mode:
 1 Insert Batteries
  a. Customer installs batteries.
  b. The Signal Processing Means enters the power up mode.
  c. The Signal Processing Means measures the battery Voltage
 2 If the battery Voltage is less than 2.2 Vdc
  a. A low Voltage alarm sounds.
  b. The LEDs blink fast.
  c. Low Battery alarm stops after 60 seconds.
 3 If low battery Voltage is detected new Batteries must be installed.
 4 If correct battery Voltage is detected
  a. The Alarm means beeps and flashes LEDs. One beep for 1 second and two short beeps 0.2 seconds.
  b. Sound level for alarms in power up mode is maximum.

Alarm Setup Mode:
 5 Once the power on test has been passed the Signal Processing Means enters the alarm configuration mode. In this mode the sound and/or vibration combination and the sound level may be selected.
 6 If the sound amplitude of the alarm sound is too low the user pushes the three way switch up to increase the sound amplitude. There are five sound amplitude levels. Four support various amplitudes of alarm sound.
 7 If the sound amplitude of the alarm is too loud the user pushes the three way switch toward the bottom of the case to reduce the amplitude. The fifth amplitude level defeats the alarm sound for vibration only.
 8 The Signal Processing Means checks for the sensor plug to be inserted into the jack. If the sensor is inserted properly the LEDs flash slowly and alarm sounds for one second. If the sensor is not inserted the LEDs flash fast and the alarm sound until the sensor is inserted.
 9 Once the alarm is setup, the user may select the monitor mode. The user may press the reset button. If the user does not press the reset button within 30 seconds of the last 3 way switch press, the Signal Processing Means will automatically begin the monitor mode.

Monitor Mode:
 10 Voltage is applied to the sensor. The Signal Processing Means checks for the presence of the sensor jack. The 3 way switch has no input to the system in monitor mode.
  a. If a dry clean sensor is inserted correctly, the LEDs flash slowly. They flash every 2 seconds for 8 seconds.
  b. If the sensor is not plugged in the LEDs flash fast with alarm tone. The user inserts the sensor jack into the Signal Processing Means alarm unit and the LEDs flash slowly. They flash every 2 seconds for 8 seconds. The unit moves into monitor mode.
 11 Once the sensor is correctly inserted, the unit monitors the sensor for moisture. The LEDs do not flash and there is no alarm sound or vibration to disturb the user. The microprocessor goes into sleep mode. This reduces current drain.

Alarm Mode:
 12 Upon the detection of moisture on the sensor, all power to the sensor is removed. This prevents any electrolysis of the urine. This feature eliminates possible irritation as the result of electrolyzed compounds.
 13 Upon detection of moisture on the sensor, the LEDs flash fast. The alarm sound is activated, if the user has not selected amplitude level five, which is vibrate only mode. If any vibration mode has been selected the unit begins to vibrate accordingly.
 14 If the user does not press the reset button, the unit continues to produce sound and/or vibration and the LEDs flash fast until the batteries are depleted.
 15 The user pushes the reset button, the sound and/or vibration ceases and the LEDs continue to flash fast. If the user does not remove and clean the sensor within five minutes, all alarms are re instituted.
 16 The user removes, cleans, and dries the sensor to remove the urine residue.
 17 The user installs the clean and dry sensor. If the sensor tests as clean, after 2 seconds the unit is in the monitor mode and the LEDs stop flashing.

DETAILED DESCRIPTION

An alarm unit including: a power source means; an electronics portion including a signal processing means; a square or rectangular plastic casing 100 surrounding the electronics portion; and a separable clip attachment means. The plastic casing has front 112 and back 110 main surfaces, left and right sides, and top and lower ends. The front main surface of the plastic casing includes two LED light housings 120 and a perforated alarm grill portion 190. The casing top end includes a recessed snooze reset button 400. The casing back includes a battery door portion 180, a rubber or silicone strip portion 140 and screw holes 160 for attaching the front half of the casing to the back half. Around the periphery of the unit runs a rubber or silicone bumper strip 140 located functionally for the purpose of protecting the electronics in the event of contact with hard surfaces as well as to seal the seam where the casing front half and back half are held against each other via screw attachment means. The casing left and right sides include small slot means 500 and a switch guard lip portion 220 for the three-way switch 200. A power source means may include batteries.

In a preferred embodiment, a large detachable plastic clip means 300 is attachable via the left and right slot means 500 on the right and left sides of the plastic casing that correspond to left and right tab means 360 on the ends of two attachment arms 340. The clip means 300 is comprised of a vertical main body portion 380 and a horizontal casing attachment portion 390 whereby the two portions are attached to each other in a perpendicular configuration with the main body upper end 325 extending above the horizontal top edge of the casing attachment portion 390 and the main body lower end 315 extending below the horizontal bottom edge of the casing attachment arm portion 340. The main body lower end portion 315 occupies a plane that is parallel to but above the plane occupied by the main body upper end 325, whereby said main body lower end plane 325 is located farther away from the casing back than that plane occupied by the main body upper end 315. The plane occupied by the main body lower end 325 being of sufficient distance from the casing back to enable using the clip on thick types of clothing such as diapers. The casing attachment portion 390 comprises two opposite attachment arms 340 that extend outward and then downward from the clip main body portion 380. On the inner surface of the downward extending portion of the attachment arms are a pair of tab means 360 that attach frictionally into slot means 500 located on the left and right sides of the casing 100.

Attached to the clip main body bottom surface lower end are a set of parallel plastic semicircular teeth 815 that extend downward from the bottom side of the main body and terminate in a tip end. A tooth bridge portion 825 extends perpendicularly to and is attached between and to said parallel teeth 815 so that said parallel teeth support said tooth bridge portion. The tip ends of said parallel teeth and bottom surface of said tooth bridge are aligned so as to form an elongated contact point 835 for crimping a portion of clothing, for example a pajama top collar 40, between said elongated contact point and a rubber strip portion 520 located permanently on the casing back. Said elongated contact point 835 is comprised of roughened plastic so that even thin portions of clothing will not slip around between the elongated contact point 835 and rubber strip 520. The distance between the clip main body The elongated contact point and the rubber strip are forced together by the positioning of the slot and tab attachment means and the clip main body upper end which lies flat against the surface of the casing back. Said positioning enables the attachment arms to act as a fulcrum, so that the clip main body upper end supports the attachment arms when said elongated contact point is lifted away from the casing back to crimp a portion of clothing against the rubber strip.

In an alternative embodiment, the clip means is not used whereby the casing back is exposed for use with other means for attaching the casing to the user's clothing. The clip remains a preferred embodiment, however, due its ease of use, robustness, use with any thickness of clothing article including diapers, and because it allows for the unit to be very easily transported from one article of clothing to another.

The signal processing means operates, in a non-limiting sense, in four interdependent modes so as to control unit operation and to properly employ certain features. Upon installment of batteries the first mode entered is the Power Up mode.

During the Power Up mode the signal processing means establishes that there is sufficient power in the batteries to activate the alarm. This low power indicator feature is implemented in the software controlling the signal processing means. Within the signal processing means there are one or more analog to digital converters. The analog to digital converter is connected to the battery Voltage through a programmed multiplexer. The output of the analog to digital converter is compared to a programmed digital word. This digital word comprises a specific number of bits. If the output of the analog to digital converter is less than that of the programmed digital word, the low power alarm is enabled including sending power to audible alarm means and light emitting means. The low power alarm has sufficient priority to interrupt other programs running on the signal processing means.

After determining sufficient power supply, the signal processing means enters Alarm Setup mode wherein the alarm settings are made using the three-way switch and wherein a switch means within the electric jack portion of the electronics portion indicates whether the 3.5 mm cable plug from the electrical cable leading to and from the analyte sensor portion has been properly inserted. The switch means is located within the 3.5 mm electric jack portion. An input pin to the signal processing means is connected to the output of the switch that is located on the 3.5 mm jack. The output of the switch is connected to a resistor which is connected to the negative supply. The switch is connected to the positive supply. When the 3.5 mm plug is inserted into the jack (analyte sensor installed) the switch is open. With the sensor plugged into the jack the output of the switch is the negative supply. If the sensor is not plugged into the 3.5 mm jack the output of the switch is connected to the positive supply. The signal processing means input pin receives either a positive supply input and enables the sensor unconnected alarm involving the light emitting means and audible alarm means. The sensor unconnected alarm is implemented in the software controlling the signal processing means.

Protruding slightly from the surface of the casing side is the three-way switch handle 200, protected all around by a switch guard portion 220 that operates as a protective lip. The switch handle is semicircular and contains ridges for easy switch manipulation with the finger and/or fingernail. The three-way switch consists of three switches. One contact of each switch in the three way switch is connected to a resistor. The other contact of each switch is connected to the positive supply. When a switch is used, a signal processing means input pin becomes connected to various voltages of different values. The programming software of the signal processing means controls the actions of the output pins with the application of the positive supply to each respective input pin. In use, the three-way switch is employed only in the Alarm Setup mode whereupon the switch is used to toggle through and select an alarm chime type and to select alarm volume with a zero volume setting of no audible alarm so that only vibrate and lights are used to alarm analyte detection. After both chime type and volume have been set using the three-way switch the signal processing means exits the Alarm Setup mode and enters Monitor mode and in doing so deactivates the three-way switch whereby the alarm settings cannot be changed accidentally.

In the Monitor mode the signal processing means waits for a change in state across electrodes located in the analyte sensor portion. Upon a change in state in the sensor electrodes (indicating presence of an analyte) the signal processing means enters Alarm mode and power is sent to the alarm means. The alarms means includes a vibrating means, a light emitting means, and an audible alarm means that are synchronized to vibrate, flash and sound at the same time and frequency. The user can set alarm chime type and volume or can choose not to use the audible alarm means by setting the alarm volume to zero in Alarm Setup mode. The light emitting means is always employed in the analyte detection alarm. A snooze reset button is employable during Alarm mode with which the user can temporarily disable the power to the alarm means by quickly depressing the snooze reset button. This feature enables the user to have enough time to wake up, see what has happened, head to and use the bathroom to urinate, clean and dry the sensor and remove the sensor cable plug before the alarm means is once again enabled. The signal processing means implements a timer that is disabled if the sensor is removed during analyte detection alarm. If the sensor is not removed the timer counts until a full count is detected at which point power to the alarm means is once again enabled. The signal processing means thereby requires a multi-step alarm shut off process forcing a user to wake up to turn off the alarm but also making it easy to temporarily disable the alarm and focus on the need to urinate.

The previous is a detailed description of illustrative embodiments of the present invention. As these embodiments of the present invention are described with references to the aforementioned drawings, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings are not to be considered in a limiting sense, as it is understood that the present invention is in no way limited to the embodiments illustrated.

What is claimed is:

1. An analyte detection and monitoring device comprising:
A signal processing means configured and arranged to actuate an alarm means whereby:
  the signal processing means and alarm means are provided power from a power source means that includes a battery;
  an arrangement of electrical components and circuit elements are arranged and configured to support the signal processing means;
  said signal processing means and said arrangement of electrical components and circuit elements are encased in a protective plastic casing that is attached to a user's clothing using a clip type attachment means;
  the signal processing means is configured and arranged to receive an input signal from an electric jack whereby a plug attached to an electrical cable is inserted into said electric jack and thereby connected to the signal processing means and whereby said electrical cable is capable of carrying an electric current through and from an analyte sensing means; and
  the signal processing means operates in different interdependent modes as a means for implementing control over alarm operation and enablement of certain alarm features including:
    a Power Up mode whereby a low power indicator means determines whether the power source means has sufficient power to operate the alarm;
    an Alarm Setup mode whereby the user can select alarm volume and alarm chime type settings and whereby it is determined whether the electrical cable plug is properly inserted into the electric jack;
    a Monitor mode whereby the signal processing means waits to detect a change in state across electrodes in the analyte sensing means; and
    an Alarm mode whereby the alarm means is activated by an appropriate input signal from the signal processing means and whereby the alarm means can be temporarily deactivated by an alarm delaying means.

2. The alarm means of claim 1 comprising:
an audible alarm means;
a vibrating alarm means;
a light emitting means including LED lights that is always employed upon analyte detection; and
a combination thereof whereby said combination may be synchronized so that said audible alarm means, vibrating alarm means and/or light emitting means are synchronized to respectively sound, vibrate and flash together at the same frequency and time.

3. The device according to claim 1 wherein the electric jack includes a switch means that includes and involves an arrangement and configuration of circuit elements that enable indication to the signal processing means whether the electric cable plug is properly inserted into the electric jack and whereby said signal processing means generates a suitable input signal to the alarm means so as to actuate said alarm means in a specific arrangement of sound, vibration and/or light or a combination thereof so as to indicate to the user whether said electrical plug is properly inserted into said electric jack and whereby the signal processing means will not enter into the Monitor mode unless said proper insertion is achieved.

4. The device according to claim 1 including the low power indicator means whereby upon detecting an insufficient level of power from the power source means the signal processing means includes and involves an arrangement and configuration of circuit elements to generate an input signal to the alarm means so as to actuate said alarm means in a specific arrangement of sound, vibration and/or light or a combination thereof so as to indicate to the user that said power source means are insufficient.

5. The device according to claim 1 including a three-way switch that is connected to the signal processing means by an arrangement and configuration of circuit elements whereby:
  the three way switch is comprised internally of three distinct switches;
  the three way switch is attached to a plastic ridged semicircular handle portion that extends somewhat outside of the casing for easy finger manipulation;
  the three way switch only functions in the Alarm Setup mode whereby it is deactivated by the signal processing means upon exiting Alarm Setup mode;
  said handle portion manipulates said three distinct internal switches by being pushed in the up, down, or inward direction in order to choose between and select alarm volume and chime type settings;

the lowest volume setting results in no audible alarm volume with lights and vibrate only; and the three way switch is deactivated when the signal processing means goes from Alarm Setup mode to Monitor mode after establishing that:
- the electric cable plug is inserted properly;
- that there is no analyte present on the analyte sensing means;
- that the power source means has sufficient power; and
- that the user has set the desired alarm settings.

6. The device according to claim 1 including the alarm delaying means wherein the alarm means is temporarily deactivated after having been activated due to presence of an analyte on the analyte sensing means during Monitor mode and whereby the alarm delaying means comprises:
- a switch with a plastic button portion that extends through the casing for external operation;
- an arrangement and configuration of circuit elements that, in use, connect said switch to the signal processing means; and
- activation of said switch by the user during Alarm mode generates an input signal from the signal processing means to a timer whereby:
  - said timer removes power to the alarm means;
  - said timer performs a full count after which power to the alarm means is restored; and
  - said timer is disabled by removal of the electric cable plug from the electric jack and then reinsertion of the electric cable plug into the electric jack after the analyte has been removed from the analyte sensing means.

7. The device according to claim 1, wherein the clip type attachment means comprises a plastic body portion and a plastic perpendicular casing attachment portion comprised in part of two equally spaced apart attachment arm portions that extend downward from the plane of said casing attachment portion and include a tab portion or portions located on the inner surfaces of said downward extending attachment arm portions whereby said tab portions face each other, and wherein the clip type attachment means comprises a set of parallel semicircular teeth at its bottom end that extend downward from the plastic body portion and that terminate in roughened plastic edges, and wherein a tooth bridge portion extends perpendicularly to and is attached between and to said parallel teeth so that said parallel teeth support said tooth bridge portion and whereby the bottom surfaces of said parallel teeth and said tooth bridge are aligned so as to form an elongated contact point for crimping a portion of clothing between said elongated contact point and a rubber or silicone strip portion located on the casing back, and wherein the plastic body portion top end and said bottom end occupy different horizontal planes whereby the distance between said planes is roughly equivalent to the size of the downward extension dimension of said teeth portions, and wherein said plastic body portion top end and said casing attachment portion lay flat against the back surface of the casing, and wherein the casing attachment portion acts as a fulcrum between said plastic body portion top end and bottom end during use of the clip type attachment means whereby the clip teeth are lifted upwards so as to receive clothing or diaper material between said teeth and the casing back surface.

8. The device according to claim 7, wherein the casing is comprised of plastic, is generally square or rectangular shaped and has rounded corners, and whereby:
- the left and right side portions of the casing each contain a recessed slot portion whereby a tab portion or portions located on attachment arms of the clip may be inserted so as to enable the left and right slot portions to frictionally attach the casing to the clip; and
- the rubber or silicone strip portion is positioned on the casing back underneath the point of contact with the clip teeth and tooth bridge.

* * * * *